(12) United States Patent
Plee et al.

(10) Patent No.: US 6,884,918 B1
(45) Date of Patent: Apr. 26, 2005

(54) AGGLOMERATED ZEOLITIC ADSORBENTS, METHOD FOR OBTAINING SAME USES THEREOF

(75) Inventors: Dominique Plee, Lons (FR); Alain Methivier, Rueil-Malmaison (FR)

(73) Assignees: CECA S.A., Puteaux (FR); Institut Francais du Petrole, Rueil-Malmaison (FR)

( * ) Notice: Subject to any disclaimer, the term of this patent is extended or adjusted under 35 U.S.C. 154(b) by 0 days.

(21) Appl. No.: 09/914,037

(22) PCT Filed: Feb. 16, 2000

(86) PCT No.: PCT/FR00/00382

§ 371 (c)(1),
(2), (4) Date: Nov. 5, 2001

(87) PCT Pub. No.: WO00/50166

PCT Pub. Date: Aug. 31, 2000

(30) Foreign Application Priority Data

Feb. 22, 1999  (FR) ............................ 99 02151

(51) Int. Cl.$^7$ ................................. C07C 7/13
(52) U.S. Cl. ................. 585/828; 585/820; 585/825; 585/827
(58) Field of Search ................. 585/820, 825, 585/827, 828

(56) References Cited

U.S. PATENT DOCUMENTS

| | | | |
|---|---|---|---|
| 589,981 A | 9/1897 | Reid et al. ................. 131/323 |
| 2,985,589 A | 5/1961 | Broughton et al. ......... 210/676 |
| 3,119,660 A | 1/1964 | Howell et al. ............... 23/112 |
| 3,558,732 A | 1/1971 | Neuzil ......................... 260/674 |
| 3,588,730 A | 6/1971 | Schreuer et al. ............. 331/2 |
| 3,626,020 A | 12/1971 | Neuzil ......................... 260/674 |
| 3,663,638 A | 5/1972 | Neuzil ......................... 260/674 |
| 3,878,127 A | 4/1975 | Rosback ....................... 252/455 |
| 3,960,774 A | 6/1976 | Rosback ....................... 252/455 |
| 4,402,832 A | 9/1983 | Gerhold ....................... 210/659 |
| 4,498,991 A | 2/1985 | Oroskar ....................... 210/659 |
| 4,633,018 A | 12/1986 | Zinnen ......................... 564/424 |
| 4,642,397 A | 2/1987 | Zinnen et al. ............... 568/934 |
| 4,642,406 A | * 2/1987 | Schmidt ....................... 585/477 |
| 4,818,508 A | 4/1989 | Flank et al. ................. 423/328 |
| 4,940,548 A | 7/1990 | Zinnen ......................... 210/656 |
| 5,149,887 A | 9/1992 | Zinnen ......................... 568/751 |
| 5,284,992 A | 2/1994 | Hotier et al. ............... 585/805 |
| 5,629,467 A | 5/1997 | Hotier et al. ............... 585/805 |
| 5,849,981 A | 12/1998 | Kulprathipanja ............ 585/828 |
| 5,919,287 A | * 7/1999 | Moreau ......................... 95/130 |
| 6,410,815 B1 | * 6/2002 | Plee et al. ................... 585/828 |
| 6,652,626 B1 | * 11/2003 | Plee ............................... 95/96 |

FOREIGN PATENT DOCUMENTS

| | | |
|---|---|---|
| EP | 0 115 068 | 8/1984 |
| EP | 0 115 631 | 8/1984 |
| EP | 0 137 063 | 4/1985 |
| EP | 0 154 855 | 9/1985 |
| EP | 0 531 191 | 3/1993 |
| EP | 0 893 157 | 1/1999 |
| FR | 2 766 475 | 1/1999 |
| FR | 2 767 524 | 2/1999 |
| JP | 5-163015 | 6/1993 |

\* cited by examiner

*Primary Examiner*—Walter D. Griffin
*Assistant Examiner*—Tam M. Nguyen
(74) *Attorney, Agent, or Firm*—Smith, Gambrell & Russell, LLP

(57) ABSTRACT

The present invention relates to agglomerated zeolitic adsorbents based on zeolite X with an Si/Al ratio such that $1.15<Si/Al\leq1.5$, at least 90% of the exchangeable cationic sites of the zeolite X of which are occupied either by barium ions alone or by barium ions and potassium ions whose Dubinin volume is greater than or equal to 0.240 $cm^3/g$.

They are obtained by agglomerating zeolite powder with a binder, followed by the zeolitization of the binder, the exchange of the ions of the zeolite by barium ions (and potassium ions) and the activation of the adsorbents thus exchanged.

These adsorbents are particularly suited to the adsorption of the para-xylene present in $C_8$ aromatic hydrocarbon fractions in the liquid phase in processes of simulated moving bed type but also to the separation of sugars, polyhydric alcohols, cresols or substituted toluene isomers.

8 Claims, No Drawings

AGGLOMERATED ZEOLITIC ADSORBENTS, METHOD FOR OBTAINING SAME USES THEREOF

TECHNICAL FIELD

The field of the invention is that of agglomerated zeolitic adsorbents based on zeolite X exchanged with barium or based on zeolite X exchanged with barium and with potassium.

BACKGROUND OF THE INVENTION

The prior art has recognized that adsorbents composed of zeolites X or Y exchanged by means of ions such as barium, potassium or strontium, alone or as a mixture, are effective in selectively adsorbing para-xylene in a mixture comprising at least one other $C_8$ aromatic isomer. U.S. Pat. No. 3,558,730, U.S. Pat. No. 3,558,732, U.S. Pat. No. 3,626,020 and U.S. Pat. No. 3,663,638 disclose adsorbents comprising aluminosilicates exchanged by barium and potassium which efficiently separate para-xylene from a mixture of $C_8$ aromatic isomers.

U.S. Pat. No. 3,878,127 discloses a method for the preparation of adsorbents intended for the separation of xylenes, which consists in treating, in sodium hydroxide solution under hot conditions, agglomerates (zeolite X+binder) with an $Na_2O/Al_2O_3$ ratio of rigorously less than 0.7, in order to replace the exchangeable cations of the zeolite (such as protons or cations from Group IIA) with sodium prior to a barium or barium+potassium exchange, the preliminary exchange with sodium allowing a larger amount of barium or barium+potassium ions to be added to the zeolitic structure.

These adsorbents may be used as adsorption agents in liquid-phase processes, preferably of simulated countercurrent type, similar to those disclosed in U.S. Pat. No. 2,985,589, which apply, inter alia, to $C_8$ aromatic fractions resulting, for example, from processes for the dialkylation of benzene in gas-phase processes.

Barium-exchanged zeolites X have numerous other applications as adsorption agents, among which may be mentioned:

the separation of sugars, see, for example, EP 115,631 or EP 115,068, the separation of polyhydric alcohols (EP 137,063), the separation of substituted toluene isomers, U.S. Pat. No. 4,642,397 (nitrotoluene), U.S. Pat. No. 4,940,548 (diethyltoluene) or U.S. Pat. No. 4,633,018 (toluenediamine), the separation of cresols (U.S. Pat. No. 5,149,887).

In the above-listed references, the zeolitic adsorbents are provided in the form of a powder or in the form of agglomerates predominantly composed of zeolite having at least 15 to 20% by weight of inert binder and their Dubinin volume measured by nitrogen adsorption at 77° K after degassing under vacuum at 300° C. for 16 h, is inferior to 0.230 $cm^3/g$.

As the synthesis of zeolites X is predominantly carried out by nucleation and crystallization of silicoaluminate gels, powders are obtained which are particularly difficult to employ on an industrial scale (significant pressure drops when the powders are handled) and granular agglomerated forms are preferred. These agglomerates, whether in the form of blocks, balls or extrudates, are usually composed of a zeolite powder, which constitutes the active component, and of a binder intended to ensure the cohesion of the crystals in the form of grains. This binder has no adsorbent property, its function being to confer on the grain sufficient mechanical strength to withstand the vibrations and movements to which it is subjected during its various uses. The agglomerates are prepared by thickening zeolite powder with a clay paste, in proportions of the order of 80 to 85% of zeolite powder per 20 to 15% of binder, then shaping as balls, blocks or extrudates and heat treating at high temperature in order to bake the clay and reactivate the zeolite, it being possible for exchange with barium to be carried out either before or after the agglomeration of the pulverulent zeolite with the binder. This results in zeolitic bodies with a particle size of a few millimeters which, if the binder is chosen and the granulation is carried out according to the rules of the art, exhibit an array of satisfactory properties, in particular of porosity, of mechanical strength and of resistance to abrasion. However, the adsorption properties are obviously reduced in the ratio of active powder to the powder and its inert agglomeration binder.

Various means have been proposed for overcoming this disadvantage of the binder being inert with regard to the adsorbent performance, including the conversion of the binder, in all or part, to zeolite. This operation is usually carried out when binders of the kaolinite family, precalcined at temperatures of between 500° C. and 700° C., are used. An alternative form consists in moulding kaolin grains and in converting them to zeolite: its principle is set out in "Zeolite Molecular Sieves" by D. W. Breck, John Wiley and Sons, New York. This technology has been applied with success to the production of grains of zeolite A or X which are composed of up to 95% by weight of the zeolite itself and of a residue of unconverted binder (see, to this end, U.S. Pat. No. 3,119,660), the addition of a source of silica being recommended when it is desired to obtain a zeolite X ("Zeolite Molecule Sieves", Breck, p. 320).

Flank et al. show, in U.S. Pat. No. 4,818,508, that it is possible to prepare agglomerates based on zeolite A, X or Y by digestion of reactive clay preforms (obtained by heat treatment of unreactive clay, such as halloysite or kaolinite, at least 50% by weight of which exists in the form of particles with a particle size of between 1.5 and 15 $\mu m$, preferably in the presence of a pore-forming agent) with an alkali metal oxide. The examples relating to the synthesis of agglomerates based on zeolite X show that it is necessary to add a source of silica, which is not the case when preparing agglomerates based on zeolite A.

JP-05163015 (Tosoh Corp.) teaches that it is possible to form grains of zeolite X with a low Si/Al ratio of less than 1.25 by mixing a zeolite LSX powder, the zeolite LSX having an Si/Al ratio of 1.25, with kaolin, potassium hydroxide, sodium hydroxide, carboxymethylcellulose. Shaping is carried out by extrusion. The grains thus obtained are dried, calcined at 600° C. for 2 hours and then immersed in a sodium hydroxide and potassium hydroxide solution at 40° C. for 2 days.

These two documents teach that it is possible to prepare mechanically strong solids. Nevertheless, the associated processes are cumbersome and suffer either from the excessive reaction time or from the number of stages involved. Furthermore, it may be feared that the heat treatment as claimed in JP-05-163015, after the shaping stage, does not contribute to the amorphization of the grain and that the object of the caustic digestion which follows is to recrystallize it, which would explain the slowness of the process.

DESCRIPTION OF THE INVENTION

The subject-matter of the present invention is agglomerated zeolitic adsorbents based on zeolite X with an Si/Al ratio such that $1.15<\text{Si/Al}\leq 1.5$, at least 90% of the exchangeable cationic sites of the zeolite X of which are occupied either by barium ions alone or by barium ions and potassium ions, it being possible for the exchangeable sites occupied by potassium to represent up to ⅓ of the exchangeable sites occupied by barium+potassium (the possible remainder generally being provided by alkali metal or alkaline earth metal ions other than barium (and potassium)) and an inert binder, characterized in that their Dubinin volume measured by nitrogen adsorption at 77° K after degassing under vacuum at 300° C. for 16 hours, is greater than or equal to 0.240 cm³/g, preferably greater than or equal to 0.245 cm³/g.

The subject-matter of the present invention is also a process for the preparation of these agglomerates which comprises the following stages:

a) agglomerating zeolite X powder with a binder comprising at least 80% by weight of clay which can be converted to zeolite and shaping, then drying and calcining, b) zeolitization of binder by the action of an alkaline solution, c) replacement of at least 90% of the exchangeable sites of the zeolite X by barium, followed by washing and drying the product thus treated, d) optionally replacement of at most 33% of the exchangeable sites of the zeolite X by potassium, followed by washing and drying the product thus treated, e) activation.

The agglomerating and the shaping (stage a)) can be carried out according to any technique known to a person skilled in the art, such as extrusion, compacting or agglomerating. The agglomeration binder employed in stage a) comprises at least 80% by weight of clay which can be converted to zeolite and can also comprise other inorganic binders, such as bentonite or attapulgite, and additives intended, for example, to facilitate agglomeration and improve the hardening of the agglomerates formed.

The clay which can be converted to zeolite belongs to the kaolinite, halloysite, nacrite or dickite family. Use is generally made of kaolin. The calcination which follows the drying is carried out at a temperature generally of between 500 and 600° C.

The zeolitization of the binder (stage b)) is carried out by immersion of the agglomerate in alkaline liquor, for example sodium hydroxide solution or a mixture of sodium hydroxide solution and potassium hydroxide solution, the concentration of which is preferably greater than 0.5M. The zeolitization is preferably carried out under hot conditions, processing at a higher temperature than ambient temperature, typically at temperatures of the order of 80–100° C., improving the kinetics of the process and reducing the immersion times. Zeolitizations of at least 50% of the binder are thus easily obtained. Washing with water, followed by drying, are subsequently carried out.

The exchange with barium of the cations of the zeolite (stage c)) is carried out by bringing the agglomerates resulting from stage b) (or d)) into contact with a barium salt, such as $BaCl_2$, in aqueous solution at a temperature of between ambient temperature and 100° C. and preferably of between 80 and 100° C. In order to quickly obtain a high degree of exchange of barium, i.e. greater than 90%, it is preferable to carry out the exchange with a large excess of barium with respect to the cations of the zeolite which it is desired to exchange, typically such that the ratio $BaO/Al_2O_3$ is of the order of 10 to 12, successive exchanges being carried out so as to achieve the minimum targeted degree of exchange of at least 90% and preferably of at least 95%. Throughout the text, the degrees of exchange are calculated in equivalents and not in molarity.

The optional exchange with potassium (stage d)) can be carried out before or after the exchange with barium (stage c)); it is also possible to agglomerate zeolite X powder already comprising potassium ions.

The activation (stage e)) is the final stage in the preparation of the adsorbents according to the invention. The aim of the activation is to fix the water content, more simply the loss on ignition, of the adsorbent within optimum limits. The activation is generally carried out by thermal activation, which is preferably carried out between 200 and 300° C.

The invention also relates to the uses of the zeolitic adsorbents described above as adsorption agents capable of advantageously replacing the adsorption agents described in the literature based on zeolite X exchanged with barium or based on zeolite X exchanged with barium and potassium, in particular in the uses listed below:

the separation of $C_8$ aromatic isomers, in particular xylenes, the separation of sugars, the separation of polyhydric alcohols, the separation of substituted toluene isomers, such as nitrotoluene, diethyltoluene or toluenediamine, the separation of cresols.

The invention relates in particular to an improvement in the process for the recovery of para-xylene from $C_8$ aromatic isomer fractions which consists in using, as adsorption agent for p-xylene, a zeolitic adsorbent according to the invention employed in liquid-phase processes but also gas-phase processes.

The desired product can thus be separated by (batch) preparative adsorption liquid chromatography, advantageously in a simulated moving bed, that is to say under simulated countercurrent conditions or under simulated cocurrent conditions, more particularly under simulated countercurrent conditions.

The operating conditions of an industrial adsorption unit of simulated countercurrent type are generally as follows:

| | |
|---|---|
| number of beds | 6 to 30 |
| number of zones | at least 4 |
| temperature | 100 to 250° C. |
| preferably | 150 to 190° C. |
| pressure | 0.2 to 3 MPa |
| ratio of the desorbent to feedstock flowrates | 1 to 2.5 |

(for example, 1.4 to 1.8 for a single adsorption unit (stand alone) and 1.1 to 1.4 for an adsorption unit combined with a crystallization unit)

| | |
|---|---|
| degree of recycling | 3.5 to 12, preferably 4 to 6 |

Reference may be made to U.S. Pat. No. 2,985,589, U.S. Pat. No. 5,284,992 and U.S. Pat. No. 5,629,467.

The operating conditions of a simulated cocurrent industrial adsorption unit are generally the same as those operating under simulated countercurrent conditions, with the exception of the degree of recycling, which is generally between 0.8 and 7. Reference may be made to U.S. Pat. No. 4,402,832 and U.S. Pat. No. 4,498,991.

The desorption solvent can be a desorbent with a boiling point lower than that of the feedstock, such as toluene, but also a desorbent with a boiling point greater than that of the feedstock, such as para-diethylbenzene (PDEB).

The selectivity of the adsorbents according to the invention for the adsorption of p-xylene present in $C_8$ aromatic fractions is optimum when their loss on ignition, measured at 900° C., is generally between 4.0 and 7.7% and preferably between 5.2 and 7.7%. Water and a small amount of carbon dioxide are included in the loss on ignition.

The following examples illustrate the invention.

EXAMPLES

These examples involve the measurement or the assessment of certain quantities characteristic of the adsorbents of the invention.

To assess the selectivity presented by the adsorbent of a process for the separation of para-xylene, a test is applied to it which allows the measurement of its separating power between para-xylene (PX) and its $C_8$ aromatic isomers (MX, OX), as well as between para-xylene and ethylbenzene (EB), which is important because some fractions may be rich in ethylbenzene but may not be rich in other $C_8$ isomers, and also between para-xylene and the desorbent, because it is just as important to have available a low PX/desorbent selectivity, a condition for the desorption to be efficient.

The test consists in immersing an adsorbent (17 g), thermally activated beforehand and cooled with the exclusion of air, in 80 g of a mixture of aromatics dissolved in 2,2,4-trimethylpentane.

The exact composition of the mixture is as follows:

| | |
|---|---|
| PX | 2% |
| MX | 2% |
| OX | 2% |
| EB | 2% |
| toluene (desorbent) | 2% |
| 2,2,4-trimethylpentane | the remainder |

The mixture is heated in an autoclave at 150° C. for 4 hours, a time sufficient to provide for adsorption equilibrium. A portion of the liquid is then withdrawn, condensed at −30° C. and analysed by gas chromatography. It is then possible to work out the concentrations in the adsorbed phase and in the non-adsorbed phase and to express the amount of para-xylene adsorbed and the selectivities for para-xylene with respect to the other aromatics and to the desorbent. The 2,2,4-trimethylpentane does not interfere with these results, not being adsorbed to any great extent. For Examples 1 and 2 hereinbelow, the desorbent employed is toluene.

The selectivity of the adsorbent thus prepared is measured according to the test described hereinbelow:

The selectivity Sel(B/A) of an adsorbent for a compound (B) with respect to a compound (A) is defined as the ratio of the concentrations of the compounds in the adsorbed phase divided by the ratio of the concentrations of the compounds in the non-adsorbed phase at equilibrium.

The equation of the selectivity is as follows:

$$Sel\ (B/A) = \frac{(B)z/(A)z}{(B)s/(A)s}$$

where (B)z and (B)s represent the concentrations of B in the zeolite and the solution respectively, where (A)z and (A)s represent the concentrations of A in the zeolite and the solution.

Example 1

Control Adsorbent

An industrial zeolite NaX, with an Si/Al ratio of 1.25 and an Na/Al ratio of 1, is agglomerated by intimately mixing 850 g of zeolite X powder (expressed as calcined equivalent), 150 g of Charentes kaolinite (expressed as calcined equivalent) and 6 g of carboxymethylcellulose (retention adjuvant intended to retain the water during the extrusion operation) with the appropriate amount of water for the extrusion. The extrudate is dried, crushed, so as to recover grains with an equivalent diameter equal to 0.7 mm, and then calcined at 550° C. under a stream of nitrogen for 2 h. Its toluene adsorption capacity, determined at 25° C. and under a partial pressure of 0.5, is 20.2%; it is interpreted as a micropore volume of 20.2/0.86=0.235 $cm^3/g$ (in the calculation of the pore volume, the relative density of the liquid phase is regarded as being identical to the relative density of the adsorbed toluene, that is to say 0.86).

This granule is exchanged by means of a 0.5M barium chloride solution at 95° C. in 4 stages. In each stage, the ratio of volume of solution to mass of solid is 20 ml/g and the exchange is continued for 4 hours each time. Between each exchange, the solid is washed several times, so as to free it from the excess salt. It is subsequently activated at a temperature of 250° C. for 2 h under a stream of nitrogen.

The degree of exchange with regard to barium is 97%, The toluene adsorption capacity is 14.8%, which equates to a micropore volume of 0.17 $cm^3/g$. The loss on ignition, an important quantity as it gives an estimation of residual water present on the adsorbent, is also measured: a loss on ignition of 4.5% is recorded here. The micropore volume, measured according to the Dubinin method by nitrogen adsorption at 77° K after degassing under vacuum at 300° C. for 16 h, is 0.22 $cm^3/g$.

Application of the selectivity test described above leads to the following results:

| Isomers | Selectivity |
|---|---|
| PX/OX | 2.25 |
| PX/MX | 2.12 |
| PX/EB | 1.77 |
| PX/Tol | 1.52 |

The amount of para-xylene adsorbed is equal to 0.054 $cm^3/g$.

Example 2

Adsorbent According to the Invention

An industrial zeolite NaX, with an Si/Al ratio of 1.25 and an Na/Al ratio of 1, is agglomerated by intimately mixing 800 g of zeolite X powder (expressed as calcined equivalent), 150 g of kaolin (expressed as calcined equivalent), 56 g of colloidal silica, sold by the company CECA under the tradename Cecasol®30 (and comprising 30% by weight of $SiO_2$ and 0.5% of $Na_2O$), and 6 g of carboxymethylcellulose with the appropriate amount of water for the extrusion. The extrudate is dried, crushed, so as to recover grains with an equivalent diameter equal to 0.7 mm, and then calcined at 550° C. under a stream of nitrogen for 2 h. Its toluene adsorption capacity, determined at 25° C. and under a partial pressure of 0.5, is 19.8%; it is interpreted as corresponding to a micropore volume of 0.23 $cm^3/g$ from the relative density of the toluene adsorbed, estimated from that for the liquid toluene.

200 g of granules thus obtained are placed in a glass reactor equipped with a jacket, which jacket is regulated at a temperature of 100±1° C., 1.5 l of an aqueous sodium hydroxide solution with a concentration of 100 g/l are then added and the reaction mixture is left stirring for 3 h. The granules are subsequently washed in 3 successive washing operations with water and then the reactor is emptied. The effectiveness of the washing is confirmed by measuring the final pH of the aqueous wash liquors, which must be between 10 and 10.5.

The toluene adsorption capacity of the granules thus obtained is determined under the same conditions as those described in Example 1: 22.5%, corresponding to a micropore volume of 0.26 $cm^3/g$, that is to say a gain in crystallinity of approximately 13% with respect to the granules of Example 1.

A barium exchange is subsequently carried out under operating conditions identical to those for Example 1, with the exception of the concentration of the $BaCl_2$ solution, which is 0.6M, followed by washing, then by drying at 80° C. for 2 h and, finally, by activation at 250° C. for 2 h under a stream of nitrogen.

The degree of exchange with regard to barium of this adsorbent is 97.4%, its toluene adsorption capacity is 16.2% and its loss on ignition is 5.2%. The micropore volume, measured according to the Dubinin method by nitrogen adsorption at 77° K after degassing under vacuum at 300° C. for 16 h, is 0.244 $cm^3/g$.

Application of the selectivity test described above leads to similar results to those obtained for the control adsorbent of Example 1; the amount of para-xylene adsorbed is equal to 0.06 $cm^3/g$.

Example 3

Comparative

A continuous liquid chromatography pilot unit is constructed comprising 24 columns in series with a length of 1 m and diameter of 1 cm, circulation between the $24^{th}$ column and the $1^{st}$ taking place by means of a recycling pump. Each of these columns is charged with the adsorbent prepared in Example 1 and the entire unit (columns+pipework+ distribution valves) is placed in an oven at 150° C.

According to the principle of simulated countercurrent chromatography, the injection of solvent, the withdrawal of extract, the injection of the feedstock and the withdrawal of the raffinate are advanced by 3 columns every 6 min cocurrentwise to the circulation of liquid: 6 columns (2 beds) are found between the injection of solvent and withdrawal of extract, 9 columns (3 beds) are found between the withdrawal of extract and injection of feedstock, three columns (1 bed) are found between the injection of feedstock and the withdrawal of raffinate and the final 6 columns are situated between the withdrawal of raffinate and the injection of solvent.

Continuous injection is carried out (expressed under ambient conditions) of 7.3 $cm^3$/min of toluene and 5 $cm^3$/min of a feedstock composed of 21% by weight of para-xylene, 17% of ethylbenzene, 44% of meta-xylene and 18% of ortho-xylene.

Continuous withdrawal is carried out of 5.4 $cm^3$/min of extract and 6.74 $cm^3$/min of raffinate.

During the first 2 periods of a cycle, the recycling pump delivers (at ambient temperature) 38.7 $cm^3$/min; it delivers 45.5 $cm^3$/min during the $3^{rd}$ period, 40.5 $cm^3$/min during the following 3 periods and 45.9 $cm^3$/min during the final 2 periods. para-Xylene is obtained with a purity of 92.2% and with a degree of recovery of 98.1%. The temperature is 150° C. and the pressure decreases from 30 to 5 bar. It is calculated that the productivity of the adsorbent is 0.034 $m^3$ of para-xylene adsorbed per $m^3$ of adsorbent per hour.

Example 4

According to the Invention

The pilot unit described in Example 3 is now operated with the adsorbent prepared in Example 2. It is observed that it is possible to obtain the same purity of para-xylene while increasing the flow rate of the feedstock entering the pilot unit up to 5.5 $cm^3$/min (i.e. an increase of 10%).

For this feedstock flow rate, the amount of desorbent introduced corresponds to a flow rate of 7.92 $cm^3$/min, the permutation time is 5.4 min and the productivity of adsorbent is 0.0374 $m^3$ of para-xylene adsorbed per $m^3$ of adsorbent per hour.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

What is claimed is:

1. Process for the recovery of para-xylene from $C_8$ aromatic isomer fractions in the liquid phase by adsorption of the para-xylene by an agglomerated zeolitic adsorbent in the presence of a desorbent the agglomerated zeolitic adsorbent comprising zeolite X and an inert binder, the inert binder containing at least 80% by weight of clay which has undergone zeolitization by the action of an alkaline solution, the zeolite X having an Si/Al ratio such that $1.15<Si/Al\leq1.5$ and having exchangeable cationic sites, wherein at least 90% of the exchangeable cationic sites of the zeolite X are occupied either by barium ions alone or by barium ions and potassium ions, the exchangeable sites occupied by potassium ions optionally representing up to ⅓ of the exchangeable sites occupied by barium ions and potassium ions, wherein the adsorbent has a Dubinin volume of greater than or equal to 0.240 $cm^3/g$, the Dubinin volume being measured by nitrogen adsorption at 77° K after degassing under vacuum at 300° C. for 16 hours.

2. Process for the recovery of para-xylene according to claim 1 of simulated moving bed type.

3. Process for the recovery of para-xylene according to claim 2 of simulated countercurrent type.

4. Process for the recovery of para-xylene according to claim 2 of simulated cocurrent type.

5. Process for the recovery of para-xylene from $C_8$ aromatic isomer fractions in the gas phase by adsorption of the para-xylene by an agglomerated zeolitic adsorbent in the presence of a desorbent, the agglomerated zeolitic adsorbent comprising zeolite X and an inert binder, the inert binder containing at least 80% by weight of clay which has undergone zeolitization by the action of an alkaline solution, the zeolite X having an Si/Al ratio such that $1.15<Si/Al\leqq1.5$ and having exchangeable cationic sites, wherein at least 90% of the exchangeable cationic sites of the zeolite X are occupied either by barium ions alone or by barium ions and potassium ions, the exchangeable sites occupied by potassium ions optionally representing up to ⅓ of the exchangeable sites occupied by barium ions and potassium ions, wherein the adsorbent has a Dubinin volume of greater than or equal to 0.240 cm$^3$/g, the Dubinin volume being measured by nitrogen adsorption at 77° K after degassing under vacuum at 300° C. for 16 hours.

6. Process for the recovery of para-xylene according to claim 1, wherein process the desorbent is toluene or para-diethylbenzene.

7. Process for the recovery of para-xylene according to claim 1, wherein, in the binder present in the agglomerated zeolitic adsorbent used in said adsorption step, the clay is selected from the group consisting of kaolinite, halloysite, nacrite and dickite.

8. Process for the recovery of para-xylene according to claim 5, wherein, in the binder present in the agglomerated zeolitic adsorbent used in said adsorption step the clay is selected from the group consisting of kaolinite, halloysite, nacrite and dickite.

* * * * *